United States Patent
Budovich et al.

[11] Patent Number: 6,023,169
[45] Date of Patent: Feb. 8, 2000

[54] ELECTRON CAPTURE DETECTOR

[75] Inventors: Vitali Lvovich Budovich; Alexei Anatolevich Mikhailov, both of Moscow, Russian Federation; Gerd Arnold, Leipzig, Germany

[73] Assignee: Bruker-Saxonia Analytik GmbH, Leipzig, Germany

[21] Appl. No.: 08/890,400

[22] Filed: Jul. 9, 1997

[30] Foreign Application Priority Data

Jul. 9, 1996 [DE] Germany ............ 196 27 620

[51] Int. Cl.⁷ .................. G01N 27/62
[52] U.S. Cl. ............ 324/464; 250/379; 324/450
[58] Field of Search ............ 324/464, 449, 324/450, 452, 455; 250/379, 382, 389

[56] References Cited

U.S. PATENT DOCUMENTS

| | | | |
|---|---|---|---|
| 3,149,279 | 9/1964 | Guild | 324/470 |
| 3,838,283 | 9/1974 | Andersson | 250/381 |
| 4,063,156 | 12/1977 | Patterson | 324/465 |
| 4,264,817 | 4/1981 | Neukermans et al. | 250/379 |
| 4,304,997 | 12/1981 | Sullivan | 250/379 |
| 4,740,695 | 4/1988 | Simpson | 250/282 |
| 5,528,150 | 6/1996 | Stearns et al. | 324/464 |

FOREIGN PATENT DOCUMENTS

| | | |
|---|---|---|
| 0184892 | 7/1985 | European Pat. Off. . |
| 375548 | 6/1973 | U.S.S.R. . |
| 8400604 | 2/1984 | WIPO . |

*Primary Examiner*—Josie Ballato
*Assistant Examiner*—Thomas Valone

[57] ABSTRACT

ECD with a non-radioactive electron source for generation of ions in a reaction chamber. The reaction chamber consists of two partial chambers, of which one is evacuated and contains the electron source, and the other contains connections for the feeding in of analysis gas as well as a collector electrode for detecting ions. The partition between the two partial chambers is permeable for electrons from the source but impermeable for gas molecules. The electron source may be a thermoemitter or a photocathode, which is irradiated from the outside through a window. In this way, contact between the analysis substance and the electron source is prevented, which increases measurement stability.

14 Claims, 2 Drawing Sheets

ELECTRON CAPTURE DETECTOR

FIELD OF THE INVENTION

This invention generally concerns the field of gas chromatography and can be used for monitoring trace substances e.g. halogenated organic compounds in the ppm range.

BACKGROUND OF THE INVENTION

Electron capture detectors (ECD) for gas chromatographs are known which have a radioactive ionization source in the form of $^{63}$Ni foil, as well as a collecting electrode and lines for feeding in and removing gas to be analyzed, e.g. in U.S. Pat. No. 4,063,156, which is referred to in its entirety.

The disadvantage of such a detector with a radioactive ionization source is that there is a risk of radioactive contamination. In this context, attempts were made to design ECDs with non-radioactive ionization sources in the reaction chamber, such as in U.S. Pat. No. 3,149,279 and USSR A.C.N. 375548, etc.

The known ECD most similar to the ECD proposed in this application consists of two partial chambers separated by a partition which is permeable for electrons. A non-radioactive ionization source with thermoemitter is attached in the first partial chamber, and the collecting electrode is contained in the second partial chamber, which is connected with lines for the feed in and removal of gas to be analyzed.

Such an ECD is known from the publication EP 0 115 495 A1 (PCT-WO84/00604).

In the known detector, the partition which is permeable for electrons is a perforated plate, through the holes of which the electrons are transferred from the first to the second partial chamber by means of a gas stream.

The disadvantage of the known detector is that contact between the gas to be analyzed and the thermoemitter cannot be completely excluded. Contact can be caused by an interruption in the gas stream which supplies the second chamber with electrons. Passage of analysis gas molecules through the perforated partition can occur, e.g. as a consequence of an increase in pressure in the second chamber to which the gas is fed if chromatography columns with a programmed gas stream are used. Furthermore, when using capillary chromatography columns, one usually tries to reduce the chamber volume to which the gas to be analyzed from the chromatography column is fed. This would lead to a reduction in the distance from the ionization source, which in turn allows diffusion of the analysis gas molecules, against the gas stream, into the first partial chamber where the electron source is located. These are possible causes for contamination of the active surface of the electron source by molecules of the gas to be analyzed. As a result of this, the background stream changes, which for its part magnifies the instability of the measurement and the errors when determining the concentrations.

The objective of this invention is to produce an ECD with a non-radioactive electron source which prevents all contact between analysis gas and the active surface of the electron source.

SUMMARY OF THE INVENTION

This objective is achieved by an ECD with two partial chambers, separated by a partition which is permeable for electrons, the non-radioactive electron source being arranged in the first partial chamber and the electrodes located in the second partial chamber together with an input and output for the analysis gas, wherein the partition consists of a layer of material which is permeable for electrons but impermeable for gas, the inside volume of the first partial chamber is evacuated and the electron source is connected to the negative pole of an accelerating voltage source.

The objective is achieved completely in this way.

Since the electron source is located in a separate, evacuated space, all contact of the gas with its surface is prevented, and uniform, controlled operation conditions always prevail. On the other hand, the transparency of the partition for electrons allows these to move into the second partial chamber, which forms a part of the gas circuit, and where molecule ions are formed by the electrons which pass through the partition reacting with the gas molecules.

In a favorable embodiment of the invention, the partition consists of a polymer material, e.g. of heterocyclic, aliphatic polymer or especially of mica. This is a particularly favorable material with high electron transparency on the one hand and sufficient gas-impermeability on the other.

To prevent any distortion of the partition due to differences in pressure, it is preferable to support it with a metal grid, made of copper for example, with low scattering and absorption of electrons.

It is preferable to coat the surface of the partition with a layer of conductive material connected to the positive pole of the accelerating voltage source. In this way ions may be accelerated toward the partition and then pass through it.

In a particularly favorable embodiment of the invention, the non-radioactive electron source consists of a thermoemitter supplied by a filament voltage source.

In a further embodiment of the invention, the non-radioactive electron source is a photocathode, a thin gold plate for example, the part of the reaction chamber with the electron source having a window made of radiation permeable material (particularly for UV light). Outside the reaction chamber, directly across from the window, there is a radiation source, preferably a UV lamp.

Preferably, the window material should consists of UVvol and the UV lamp should emit in the spectral range between 220 nm and 400 nm.

A preferred embodiment of the suggested detector is characterized in that an additional accelerating electrode, connected to the accelerating voltage source, is provided between the electron source and the partition.

The above mentioned features of the suggested detector completely avoid all contact between the analysis substance and the active surface of the non-radioactive electron source and thereby improve measurement stability.

Further advantages of the invention can be seen in the description and the attached drawing. The features named above and those further developed according to this invention can also be applied either individually or combined as required. The described embodiments are not intended as a conclusive listing, but are rather of an exemplary nature.

BRIEF DESCRIPTION OF THE DRAWINGS

The invention is described and explained more closely as represented in the drawing and using concrete examples. Shown are.

DESCRIPTION OF THE PREFERRED EMBODIMENTS

Figure 1:
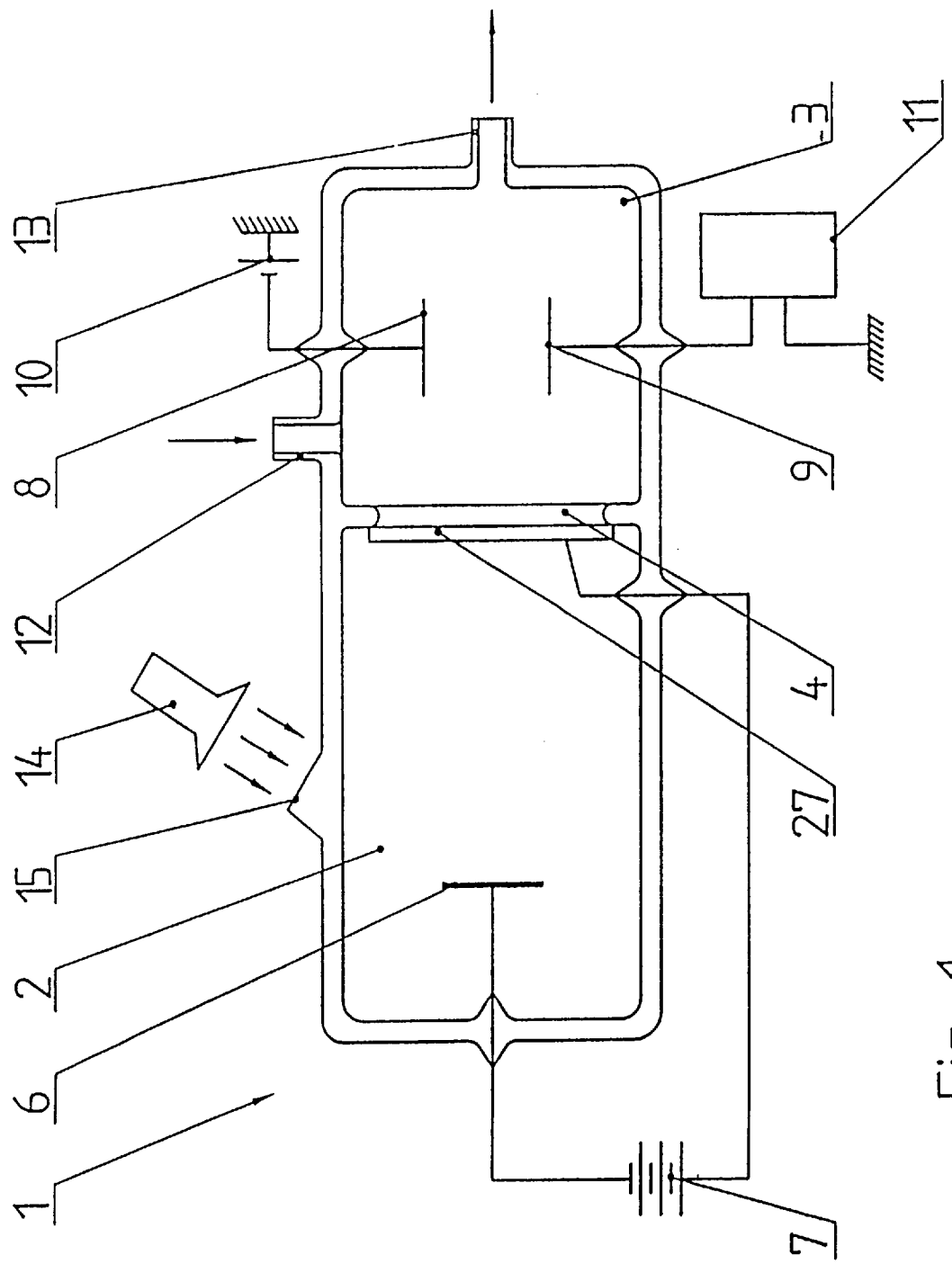
FIG. 1 a longitudinal section through a suggested ECD of a first embodiment with a photocathode as the electron source.

The ECD in the embodiment shown in FIG. 1 consists of a chamber 1, divided into two partial chambers 2 and 3, separated by a partition 4 made of material permeable for electrons and impermeable for gas, e.g. mica. The inside volume of partial chamber 2 is evacuated and a non-radioactive electron source 6 in the form of a photocathode is installed there. To avoid all distortion due to the pressure difference between partial chambers 2 and 3, partition 4 is supported by a metal grid 27, which has a geometric transmission coefficient (ratio between open and covered surfaces) of greater than 60%. Partition 4 has a thickness between 3 and 5 micrometers. The surface of partition 4 facing partial chamber 2 may also be covered by a layer of conductive material, e.g. aluminum, which then replaces grid 27. The thickness of this layer is 0.03 to 0.05 micrometers. The FIG. 1 embodiment uses a photocathode 6 (e.g. a multialkaline cathode) preferably in the form of a thin gold plate connected to the negative pole of an accelerating voltage source 7 as a non-radioactive electron source. In the housing of partial chamber 2 of chamber 1, which is preferably made of glass, a window 15 made of radiation permeable material (particularly UV) is located opposite to photocathode 6. Outside the housing of partial chamber 2, a radiation source 14 is attached opposite from window 15. Radiation source 14 is a UV lamp, which preferably emits in the range from 220 nm to 400 nm. The window in this area is radiation permeable and preferably made of UV-vol.

The radiation from source 14 penetrates window 15, falls onto photocathode 6 and generates an electron emission from the surface. The electrons are accelerated by the electric field generated by the accelerating voltage source 7 to such an extent, that they collect enough energy to move through partition 4 into the inside volume of partial chamber 3, where they interact with the molecules to be analyzed.

A polarization electrode 8, which is connected to a supply voltage source 10, and a collector electrode 9 connected to an electrometer 11, are installed in partial chamber 3. Through a feed line 12, partial chamber 3 can be supplied with gas, for example from the output of a chromatography column (not shown). Through a further line 13, the gas can again be removed.

The above detector operates in the following manner. As a result of the photoelectric effect, photocathode 6 emits electrons which, due to the potential difference (18–25 kV) between the photocathode and grid 27, are accelerated toward grid 27. Influenced by the accelerating voltage, the electrons receive enough energy to pass through partition 4 and enter partial chamber 3. Analysis gas is supplied to partial chamber 3 through feed line 12. If molecules from electrophilic substances are present in the analysis gas which thereby attach electrons, the electrical current (signal) tapped at collector electrode 9, amplified by electrometer 11, is changed in proportion to the concentration of these molecules.

Figure 2:
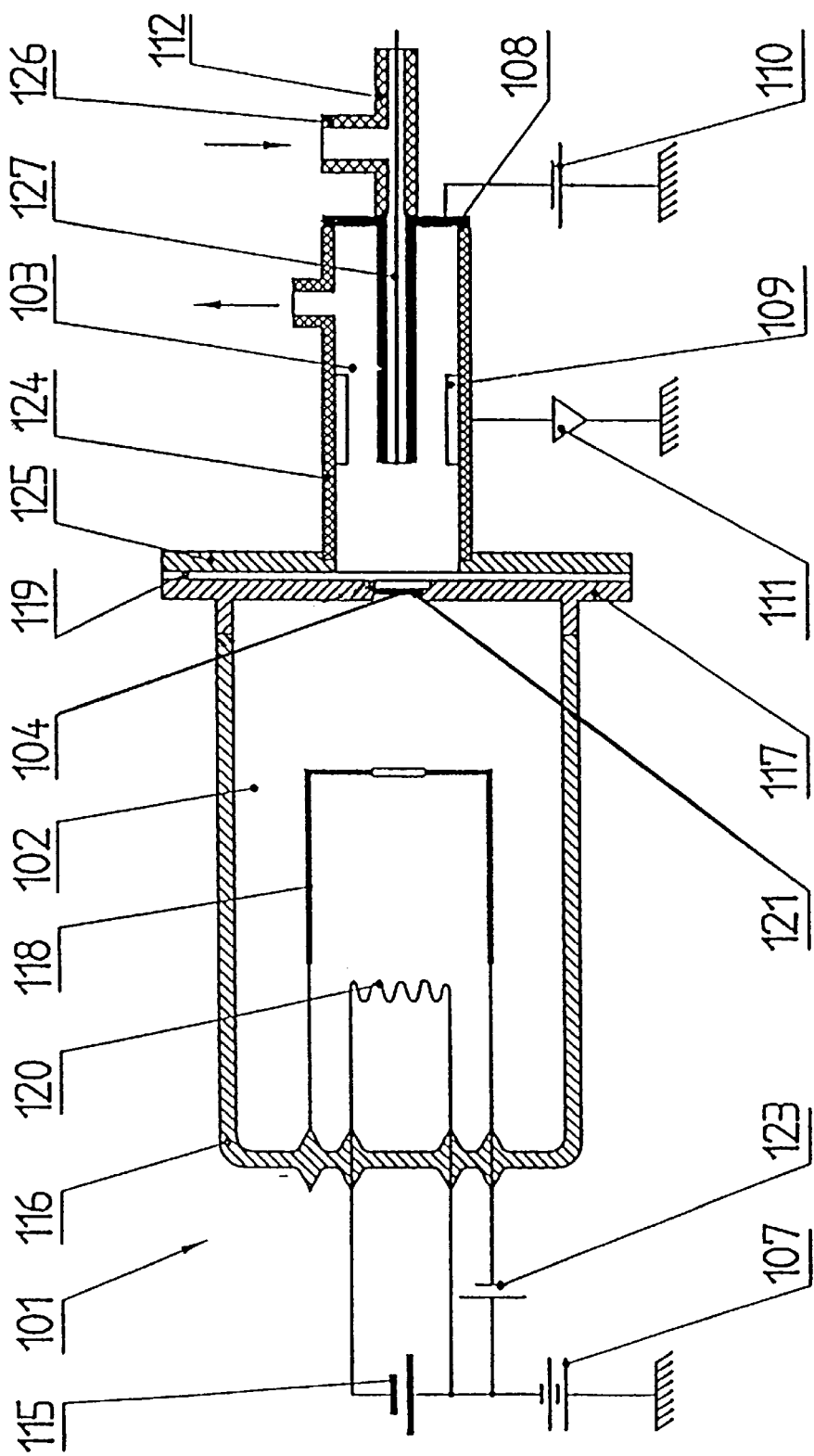
FIG. 2 a longitudinal section through a suggested ECD of a second embodiment with a thermoemitter as the electron source with two separable partial chambers.

The embodiment in FIG. 2 differs from that in FIG. 1, insofar as the housing of chamber 101 makes it possible to separate partial chambers 102 and 103. Partial chamber 102 consists of a glass cylinder 116, one end of which is connected via a vacuum connection to a metallic ring flange 117. The electron source 120 is a thermoemitter connected to an accelerating voltage source 107 and a filament voltage source 115. In partial chamber 102, there is a voltage modulator 118 which is connected to the accelerating voltage source 107 via an additional constant voltage source 123. Partial chamber 103 has a cylindrical housing 124 made of electrically insulating material, e.g. ceramic, one end of which is connected hermetically with a metallic ring flange 125. Between flange 125 and partition 104 is a sealing ring 119, e.g. made of rubber. Metal flanges 117 and 125 for partial chambers 102 and 103 are pressed together firmly to create a hermetic seal in the area of their contact with the material of partition 104, which is coated with a grounded layer 121 of conductive material, e.g. aluminum. The input 112 for the gas supply consists of a metal capillary connected to a ring-shaped polarization electrode 108, which for its part is hermetically joined to one end of partial chamber 103. The output of a capillary chromatography column 127 is inserted into the inside tube of input 112. This input 112 is connected tight to the T-flange 126, which allows the supply of a gas such as hydrogen, helium, nitrogen, etc. The embodiment in FIG. 2 is characterized by the fact that it can operate in conjunction with capillary chromatography columns which require a small inside volume of partial chamber 103. A further characteristic of this embodiment is the use of the thermoemitter 120 (i.e. an electrically heated coil) as a non-radioactive electron source. The electrons emitted from the surface of the thermoemitter 120 (which is heated via filament voltage source 115) are accelerated in the field generated by the accelerating voltage source 107 and the additional constant voltage source 123 between modulator 118 and thermoemitter 120 to such an extent that their energy is sufficient to penetrate partition 104 and enter the inside volume of partial chamber 103.

The ECD of this embodiment operates as follows:

The coil of thermoemitter 120 is heated by current from the filament voltage source 115 and emits electrons. The sources 107 and 123 generate a potential difference between the thermoemitter 120 and the additional accelerating electrode 118, which for its part accelerates the electrons within the evacuated volume of partial chamber 102 of reaction chamber 101 toward partition 104, whereupon these electrons absorb enough energy to penetrate partition 104 and pass into the other partial chamber 103. In the inside volume of the other partial chamber 103, the electrons interact with the molecules of a substance to be analyzed which are fed in the gas stream through feed line 112. If molecules from electrophilic substances which capture electrons are present in the analysis gas, the current (signal) derived from the collecting electrode 109 and amplified by electrometer 111 is proportional to the concentration of these molecules.

Components of the ECD in FIG. 2, which for the most part have the same function as those in FIG. 1, are identified with reference numbers increased by 100. It is understood that individual components or component combinations from both selected examples which have the same functions, may be exchanged one for another without leaving the scope of the invention.

The claimed invention is:
1. Electron capture detector (ECD) comprising:
   a reaction chamber comprising first and second partial chambers, an inner volume of the first partial chamber being evacuated;
   a non-radioactive electron source installed in the first partial chamber;
   an accelerating voltage source that accelerates electrons from the electron source toward the second partial chamber, a negative pole of the voltage source being connected to the electron source;
   an input line that feeds an analysis substance into the second partial chamber;

an output line through which the analysis substance is removed from the second partial chamber;

a collector electrode located in the second partial chamber; and a partition separating the first partial chamber and the second partial chamber, the partition comprising a layer of material permeable to electrons but impermeable to gas.

2. ECD as in claim 1, wherein the partition is made of mica.

3. ECD as in claim 1, further comprising a metal grid supporting the partition.

4. ECD as in claim 1, wherein the partition has a surface coated with a layer made of conductive material.

5. ECD as in claim 1, wherein the non-radioactive electron source comprises a thermoemitter supplied by a filament voltage source.

6. ECD as in claim 1, wherein the non-radioactive electron source comprises a photocathode, the first partial chamber has a housing with a radiation permeable area, and a radiation source is located outside the reaction chamber.

7. ECD as in claim 1, wherein an accelerating electrode is located between the electron source and the partition and is connected to the accelerating voltage source.

8. ECD as in claim 2, further comprising a metal grid supporting the partition.

9. ECD as in claim 8, wherein the partition has a surface coated with a layer made of conductive material.

10. ECD as in claim 9, wherein the non-radioactive electron source comprises a thermoemitter, supplied by a filament voltage source.

11. ECD as in claim 9, wherein the non-radioactive electron source comprises a photocathode, the first partial chamber has a housing with a radiation permeable area, and a radiation source is located outside the reaction chamber.

12. ECD as in claim 10, wherein an accelerating electrode is located between the electron source and the partition and is connected to the accelerating voltage source.

13. ECD as in claim 11, wherein an accelerating electrode is located between the electron source and the partition and is connected to the accelerating voltage source.

14. Method for analysis of impurities in gases using an ECD with a reaction chamber having first and second partial chambers, a non-radioactive electron source installed in the first partial chamber and an output line and a collector electrode located in the second partial chamber, the method comprising:

evacuating an inner volume of the first partial chamber;

providing an accelerating voltage source that accelerates electrons from the first partial chamber toward the second partial chamber;

electrically connecting the electron source to a negative pole of the accelerating voltage source; and separating the first partial chamber and the second partial chamber with a partition that is permeable to electrons but impermeable to gas.

* * * * *